United States Patent [19]
von Heitlinger

[11] 3,931,732
[45] Jan. 13, 1976

[54] SHARP EDGE TESTER
[75] Inventor: Eugene von Heitlinger, Chicago, Ill.
[73] Assignee: Schwinn Bicycle Company, Chicago, Ill.
[22] Filed: Oct. 24, 1974
[21] Appl. No.: 517,464

[52] U.S. Cl. .................................. 73/104; 73/78
[51] Int. Cl.[2] .................................... G01N 19/00
[58] Field of Search .......................... 73/104, 78

[56] References Cited
UNITED STATES PATENTS

| | | | |
|---|---|---|---|
| 2,335,235 | 11/1943 | Clifton | 73/78 |
| 2,472,994 | 6/1949 | Vars | 73/104 |
| 2,620,654 | 12/1952 | Campbell | 73/78 |
| 3,289,458 | 12/1966 | Deichert et al. | 73/78 X |

Primary Examiner—Charles A. Ruehl
Attorney, Agent, or Firm—McCaleb, Lucas & Brugman

[57] ABSTRACT

A hand held tool for testing the sharpness of edges to determine the presence or absence of a safety hazard in which a rotatable mandrel is driven by a torque spring at a specified velocity for a single rotation, the mandrel carrying a covering of testing material which is engaged with an edge to be tested, and having means for automatically driving the mandrel in the presence of predetermined contact force or pressure between the test material and the test edge. Means are also included for adjustably regulating the mandrel speed of rotation and the contacting pressure requisite to effect its testing operation.

12 Claims, 5 Drawing Figures

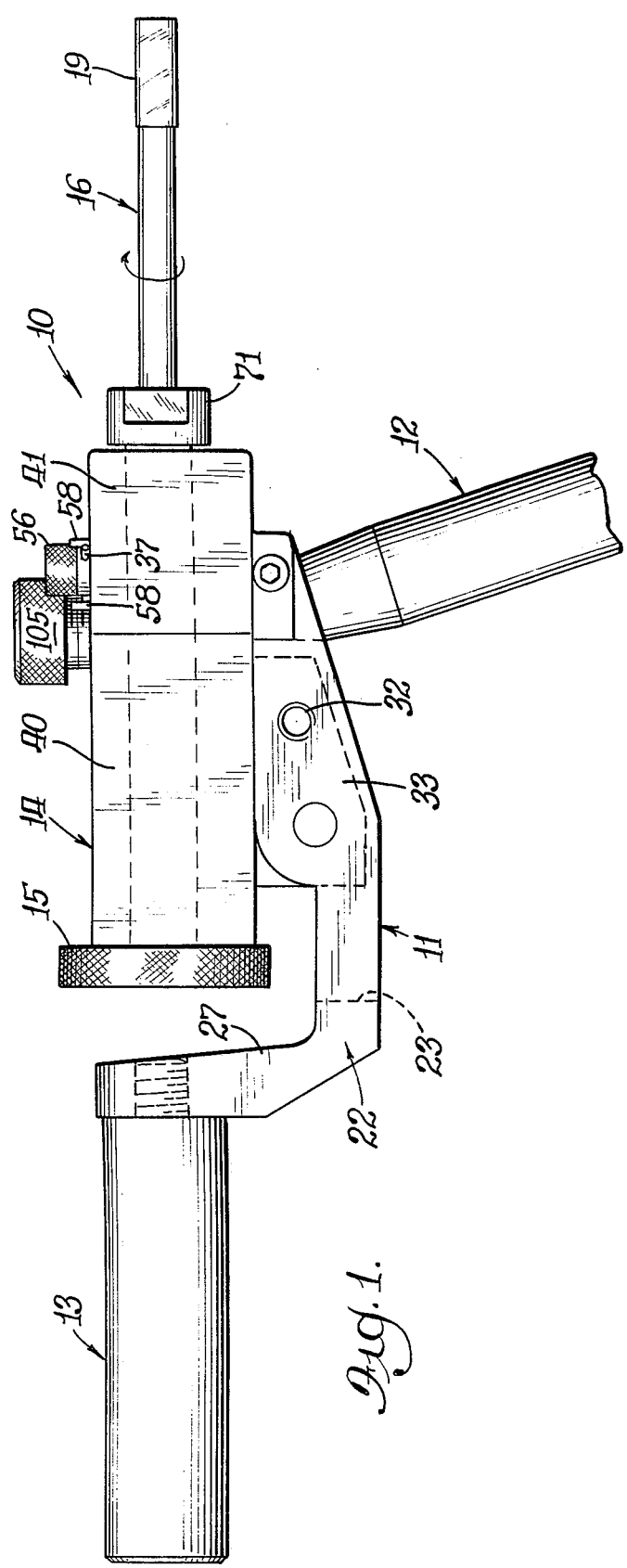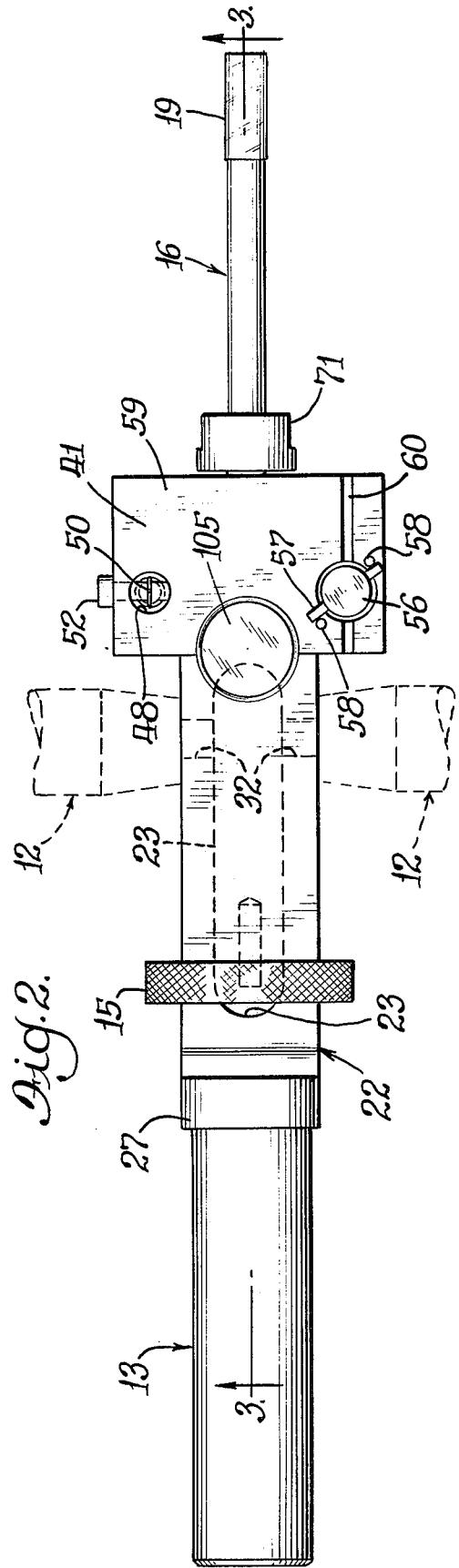

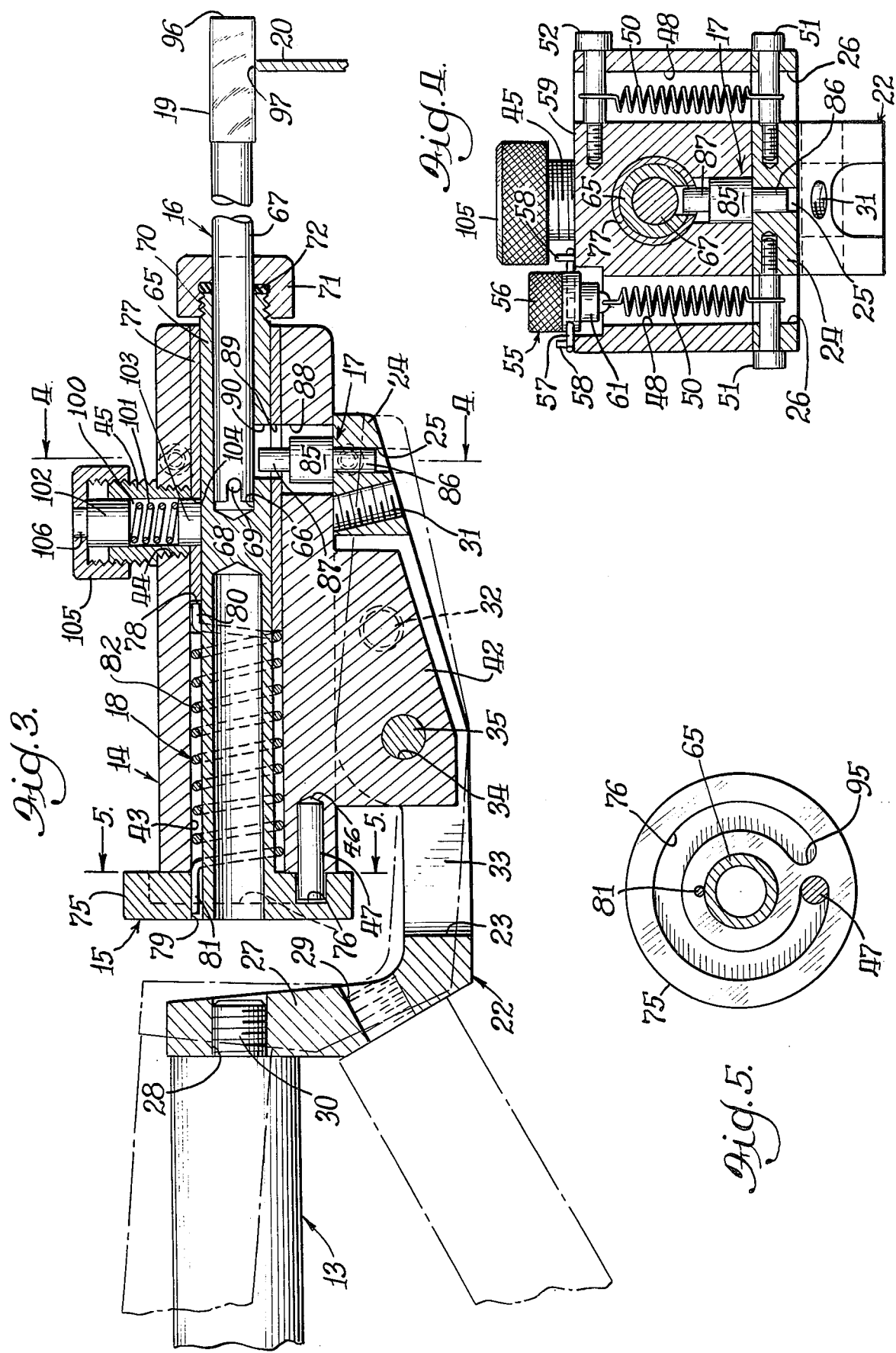

SHARP EDGE TESTER

BACKGROUND OF THE INVENTION

In recent times there has been an ever increasing social awareness of the need to protect the consuming public against hazardous substances and products. In response to this demand, the Federal Government has instituted appropriate agencies to promote product safety having regulatory powers to require the manufacture of a wide range of products under specified safety regulations and standards. Prominent among such regulated products are those normally used by children. Toys and bicycles, for example, are now subject to certain manufacturing and performance standards designed to promote the safety and welfare of the user. Among these is a prohibition against metal edges or other sharp parts on a bicycle or its components and attachments that are or may be exposed to hands or legs. A sharp edge is generally defined under the current rules as any edge that will cut through a single layer of test tape supported on a cylindrical surface of specified diameter and held in contact with the edge to be measured with a particular contacting force while the tape is moved over the edge at a specified velocity for a limited time. In view of these rules and regulations, the need has arisen for a simple testing tool capable of measuring the sharpness of an edge within the above parameters and it is to such a tool that the present invention is directed.

SUMMARY OF THE INVENTION

The present invention relates generally to hand tools and more specifically to apparatus for testing the sharpness of edges. In brief, the improved tool of this invention comprises a hand supported cradle which pivotally carries a spindle rotatably driven by motor means. the spindle has a mandrel portion for supporting a length of the test tape. Manually engageable means are provided for energizing the motor and limiting its rotational driving of the spindle. Latching means serve to lock the spindle in a loaded or "cocked" condition until selective release thereof is effected by the application of predetermined engagement force or pressure between the mandrel mounted test tape and an edge to be tested. Such predetermined contact pressure is regulated by spring means determinative of the force required to release the latch means, and additional means are provided for regulating the rotational velocity of the test tape over the edge to be tested.

It is a major object of this invention to provide an improved testing tool for determining the presence of sharp edges detrimental to the health, safety and welfare of a human.

Another object of this invention is to provide an improved testing tool, as aforesaid, which includes means for rotatably driving a length of testing material over a test edge under predetermined engagement pressure and velocity.

A still further object of this invention is to provide such a test tool having means for regulating the engagement pressure between the testing material and a sharp edge as well as the speed of movement of the testing material over such edge.

Having thus described the present invention, the above and further objects, features and advantages thereof will be recognized by those familiar with the art from the following description of a preferred embodiment thereof illustrated in the accompanying drawings and representing the best form presently contemplated so as to enable those familiar with the art to make and practice this invention.

IN THE DRAWINGS:

FIG. 1 is a side elevational view of the improved testing tool of this invention;

FIG. 2 is a top plan view thereof;

FIG. 3 is a cross sectional view taken substantially along section line 3—3 of FIG. 2 and looking in the direction of the arrows thereon;

FIG. 4 is another sectional view taken substantially along vantage line 4—4 of FIG. 3 and looking in the direction of the arrows thereon; and FIG. 5 is an additional cross sectional view taken substantially along vantage line 5—5 of FIG. 3 and looking in the direction of the arrows thereon.

Turning now to the particulars of the preferred embodiment of this invention illustrated in the accompanying drawings, initial reference is made to FIG. 1 whereat the testing tool is designated generally at 10. As there shown, tool 10 comprises cradle means 11, having plural manually engageable handle means 12 and 13 detachably joined thereto. A body member 14 is pivotally supported on the cradle means 11 and rotatably carries barrel means 15 having a spindle 16 extending outwardly at one end thereof. Latch means 17 cooperates between the cradle and barrel means to effectively release the latter for limited rotation under the driving force supplied by a motor means 18 (see FIG. 4) when predetermined engagement pressures occur between test material 19, mounted about the outer end of the spindle, and an object 20 to be tested.

With particular reference now to FIGS. 1 through 4 of the drawings, features of the cradle means 11 will be described. Shown best in FIG. 1, the cradle means comprises a unitary metal member having an elongated base body portion 22 distinguished by elongated central opening 23 therethrough (see FIGS. 2 and 3). The outer or right hand end of the body portion 22 is integral with a crosshead portion 24 (see FIG. 4) having a central opening 25 and two larger openings 26, 26 laterally, outward of central opening 25, for purposes which will appear presently.

The opposite or rear end of body portion 22 is formed integraly with a rear wall portion 27 provided with a pair of threaded openings 28 and 29 (see FIG. 3); each receptive of a cylindrical handle member 13 having a threaded stud portion 30 at one end thereof for engagement with one of the openings 28 or 29 as selected. In similar fashion the crosshead portion 24 of the cradle is provided with an angularly aligned threaded bore 31 (see FIG. 3) which is normally receptive of a second manual engageable handle means 12 which is also fittable into either of two auxiliary bored openings 32 formed through the spaced side wall portions 33 of the cradle body portion 22 formed by the central opening 23 (see FIGS. 1 and 2). Between the auxiliary openings 32 and the rear wall portion 27 and substantially central of the side wall portions 33, 33 are a pair of coaxially aligned transverse pivot openings 34 receptive of a central pivot or trunnion pin 35 whereby the cradle is pivotally attached to the body member 14 in assembly. It will be recognized and understood, of course, that the positioning of the handle members 12 and 13 is optional at the selection of the operator for his convenience in manually gripping and holding the tool in operating position.

Body member 14, best shown in FIGS. 1, 2 and 3, is, as previously noted, pivotally supported by the cradle means 11, and more specifically on the trunnion pivot pin 35. As shown best in FIGS. 1 and 2, the body member 14 comprises a generally T-shaped unitary metal member having an elongated barrel portion 40 integral with a transversely related crosshead portion 41 at its outer end; portion 41 being dimensioned to conform in plan view with the crosshead portion 24 of the cradle which it is adapted to superimpose in assembly. Depending centrally from beneath the elongate barrel portion 40 is a single trunnion portion 42 (see FIG. 3) having a suitable opening therethrough for coaxial alignment with the trunnion pin 35 between the two wall portions 33 of the cradle to pivotally interconnect those two elements. In this respect it will be noted that the central elongated opening 23 of the cradle receives the elongated trunnion support portion 42 with considerable lengthwise clearance but with relatively close fitting lateral clearance (see FIG. 2).

Body member 14 is formed with a central axially extending bore forming a barrel chamber 43, as best shown in FIG. 3 of the drawings, which is receptive of the barrel means 15 in assembly. In addition to the central axial opening 43, the body member also is provided with a cylindrical opening 44, transversely communicating with opening 43 and receptive of a threaded plug member 45, for reasons which will be amplified in greater detail hereinafter.

At its rearward end, the body member 14 is formed with a blind bore socket 46 receptive of a stop pin 47 which cooperates with barrel means 15 to limit its rotation as will be described hereinafter (see FIG. 3).

Extending through the crosshead portion 41 and symmetrically outwardly of a central vertical plan through the body member 14, as oriented in the illustrated case, are a pair of cylindrical openings 48, 48 (FIG. 4) which coaxially align with the openings 26, 26 of the cradle cross end portion 24 in assembly of the tool elements. Such openings, as best shown in FIG. 4, receive spring means 50, 50, one on each side of the barrel means 15, as illustrated. The lower end of each of the spring elements 50 is fastened to a lower tap screw 51 or like fastening means, extending across openings 26, 26 of the cradle crosshead portion, while the upper ends of such spring elements are optionally fixed to an upper tap screw 52, one extending across the upper end of each opening 48 (illustrated in the right hand side of FIG. 4) or preferably to adjustment means 55 for regulating the tension of the spring elements 50.

With specific reference now to FIGS. 2 and 4, the adjustment means 55 will better be understood as comprising a knurled, manually engageable knob having pin means 57 extending diametrically therethrough for interfering engageement with spaced pin means 58 protruding outwardly of the upper wall or face 59 of the crosshead portion 41 on opposite sides of each opening 48. A semicylindrical groove 60 (see FIG. 2) is formed inwardly of the upper wall 59 for receiving the pin means 57 at the selective rotational positioning of the knob member 56. Extending coaxially beneath the outer knurled end of the knob member 56 is a spring retaining projection comprising a cylindrical ear portion 61 (see FIG. 4) having an opening through which the upper end of the spring 50 is attached. By this expedient, it will be readily appreciated that positioning of the adjusting knob 56 so as to engage the crosshead upper face 59 and projecting pin elements 58, as illustrated in FIG. 4, effects increased tension loading of the spring element 50 associated therewith. Alternatively, rotating the knob 56 so that pin 57 thereon enters the groove 60, diminishes the tension load on the spring element therebeneath. In this manner regulation of the force of reaction exerted by springs 50 to pivotal separation of the body member 14 relatively to the cradle 11 or vice versa, as the case may be, is achieved. It will be understood that if the fixed spring retaining screws 52, 52 (as shown in the alternate version of the right hand side of FIG. 4 are employed) the adjustable regulatory tensioning of the spring elements 50 is unavailable except by the selection of spring size and characteristics.

The two springs 50, 50 serve to resiliently hold the body member 14 tightly against the crosshead portion 24 of the cradle in the manner illustrated in FIGS. 1 and 3. Pivotal movement of the body member relative to the cradle, on the other hand, requires further tensioning of the spring elements 50 requisite of the predetermined force which is utilized in the operation of the test tool of this invention to determine the force of engagement between the test material 19 and a test edge of an object to be tested.

Turning now to the features of the barrel means 15, reference is made to FIGS. 3, 4 and 5 of the drawings. As there shown, means 15 comprises an elongated cylindrical barrel body 65, coaxially mountable within the barrel chamber 43 of the body member 14. The muzzle or outer end of the barrel body 65 is bored axially inwardly to provide a cylindrical socket 66 receptive of the cylindrical shank 67 of the spindle 16; the inner end of which is slotted as at 68 to connect with a pin 69 extending across the inner end of socket 66. The outer end of the barrel body 65 is externally threaded at 70 to receive an internally threaded cap 71 carrying a compression ring 72 adapted to receive shank 67 of the spindle means therethrough. Tightening of the cap 71 on the threads 70 serves to press the ring 72 against the side walls of the spindle shank 67 and frictionally lock the same to the barrel body with the pin connection 69 serving to rotatably drive the spindle with the barrel body in operation.

The breach or rear end of the barrel body 65 is formed integrally with or affixed to a cylindrical cocking wheel 75 positioned immediately adjacent the rear end of the body member 14. As best shown in FIG. 5 of the drawings, wheel 75 is formed with a cam track 76 in the form of a discontinuous groove of generally circular formation on the inner face of the wheel member 75, such groove being receptive of the stop pin 47 in assembly. Engagement of the pin 47 and the ends of groove 76 serves to limit the rotational movement of the wheel 75 and thus the attached barrel body 65.

In order to rotatably support the barrel 65 within the barrel chamber 43, a cylindrical liner member 77 is pressed into the forward end of the barrel chamber 43 to provide bearing support for the barrel body 65. The rear or breach end of the liner 77 is slotted with opening 78, normally aligned in assembly with a cylindrical opening 79 in the wheel 75. Openings 78 and 79 receive opposite end portions 80 and 81, respectively, of a torsion spring 82 comprising, in the particular embodiment shown, the drive motor means 18. From this arrangement it will be understood that rotational movement of the wheel 75 serves to load the spring means 82 by carrying end portion 81 of such spring while the opposite end portion 80 thereof remains fixed to the liner member 77.

In order to load the torsion spring member for selected driving of the barrel body as previously noted, latch means 17 is provided, comprising a cylindrical latching stud member 85 having a reduced cylindrical portion 86 at one end press fitted into the central opening 25 in the cradle crosshead portion 24 as best seen in FIG. 4. The opposite ends of the latching stud is likewise formed with a reduced cylindrical latch projection 87 which extends upwardly through latch chamber 88 formed in the crosshead portion 41 of the barrel member and through a registered opening 89 in the liner member 77 to engage a latch opening 90 in barrel body 65. Positioning of opening 90 in the barrel body is such that latch portion 87 of the latch stud enters opening 90 when the stop pin 47 is engaged with end 95 of the cam track 76 (see FIGS. 3 and 4). By this arrangement, predetermined torsion loading of spring member 82 is required to effect substantially one revolution of the barrel body in order for the latch opening 90 to be aligned for engagement with the latch portion 87 of the latch stud. Conversely, release of the latch stud, as by withdrawing the same from the latch opening 90, permits reverse driving rotational movement of the barrel body under the influence of the drive motor means comprising the torsion spring 82. The released condition of the latch stud is indicated in dotted lines in FIG. 3 of the drawings.

Rotational driving of the barrel body 65 serves to rotatably drive the spindle means 16 because of the latter's connection with the pin 69 in the barrel chamber 66. In order to effectively utilize this driving rotational movement of the spindle means to the test functioning of the tool of this invention, the outer end of the spindle is formed with an enlarged mandrel portion 96 of cylindrical formation and of specified diameter to support a single layer of test material 19, such as Teflon tape having an adhesive backing, for engagement with the sharp edge 97 of the test object 20 as illustrated in FIG. 3. It will thus be recognized that depending on the driving force exerted by the drive motor 18, the velocity of rotation for the mandrel portion 96 and thus the tape 19 is effectively determined, while the number of revolutions thereof is determined by the length of the cam track 76 and the engaging stop pin 47. In order to effectively release the barrel end spindle for rotational testing movement in the presence of predetermined engagement forces between the tap and edge 97, the operator presses the mandrel portion with the test tape 19 thereon against the test edge with a downward force. This loads the springs 50, 50 which resiliently intertie the cradle and body member 14 and resist their relative pivotal movement. In the presence of sufficient downward pressure the resulting pivotal relative motion between the cradle and the body member 14 withdraws the latch portion 87 from the latch opening 90 and releases the barrel body 65. Upon full withdrawal of the latch stud, the barrel body is released for rotational driving action in response to the forces supplied by the torsion spring 82; such release for rotation taking place upon the occurrence of predetermined force of engagement between test tape 19 and the sharp edge 97 on the test object 20. Regulation of such engagement force between the test tape and the edge to be tested is effectively adjusted by the positioning of the spring adjusting means 55 as previously described. If the fixed mounting arrangement as provided by the spaced studs 51, 52 of the alternate arrangement illustrated in FIG. 4 of the drawings is employed, then such force may be regulated by the judicious selection of the size and characteristics for springs 50. It will thus be recognized that the tool as described to this point effectively provides a means for rotatably driving a test tape over a test edge at a predetermined velocity and under predetermined regulated engagement pressure for a selected number of revolutions (in this case a single revolution or substantially so) in accordance with the test requirements set forth heretofore. Briefly, if the tape is ruptured or cut through, an unsafe edge exceeding a predetermined maximum sharpness value is present. Conversely, failure to cut through the tape signifies a safe edge having a sharpness at or below the predetermined maximum safe value.

In addition to the basic characteristics of the tool as thus far described, it has been found desirable to provide means for regulating the rotational velocity of the barrel means 65 and thus the test tape 19. In order to effectuate this, adjustable brake means are provided and will now be described, referring to FIG. 3 of the drawings. It will be recalled that the body member 14 is equipped with a threaded plug 45 which fits into opening or bore 44 (see FIG. 3). Plug 45 has a hollow interior chamber 100 in which a compression spring 101 is carried between a cylindrical plug 102 and brake shoe 103; the latter extending through an opening 104 in the bearing sleeve member 77 to engage the external surface of the barrel body 65. A threaded cap 105 receives a hub portion 106 of the upper plug member 102 so that the cap may rotate on the external threads of the plug member 45 relative thereto, with the threaded positioning of the cap serving to regulate the braking force of engagement between the shoe 103 and the exterior of the barrel body 65. In this fashion, depending on the dragging effect of the brake shoe, the rotational velocity or speed of the barrel member in response to the spring motor means may be regulated and adjusted to accordingly regulate the velocity of the test tape over the sharp edge.

Having thus described in the preferred embodiment of this invention illustrated in the accompanying drawings, it will be appreciated that the objectives of this invention have been carried out thereby and that the same is susceptible to variations, change or substitutions of equivalents without necessarily departing from its teachings and concepts defined in the hereinafter appended claims.

The embodiments of the invention in which an exclusive property or privilege is claimed are defined as follows:

1. A tool for testing edge sharpness by moving standard test material over a test edge under predetermined velocity and engagement forces comprising: rotatably supported barrel means, means driven by said barrel means having a portion for supporting the test material in engagement with the test edge, motor means for driving said barrel and driven means at predetermined velocity, latch means holding said barrel means against rotation, and means operably responsive to predetermined engagement force between the test material and test edge for automatically operating said latch means to release said barrel means to the driving action of said motor means whereby cutting of said test material by said test edge establishes the presence of edge sharpness exceeding a predetermined safe value.

2. The combination of claim 1 and cradle means pivotally supporting said barrel means, wherein said means for operating said latch means comprises tension spring means connected to said barrel and cradle means to yieldably oppose pivotal relative movement thereof, and said latch means extends between said cradle and barrel means and is releasably operable with and upon predetemined relative movement between said cradle and barrel means.

3. The combination of claim 1 wherein said motor means comprises a torsion spring operable to rotate said barrel means, and means for loading said torsion spring with predetermined torque to drive said barrel means at predetermined velocity.

4. The combination of claim 3 and means for limiting the rotation of said barrel means.

5. The combination of claim 1 and means for adjustably regulating the rotational velocity of said barrel means.

6. A hand tool for determining the presence or absence of a safe edge having predetermined maximum sharpness comprising: cradle means having manually engageable handle means thereon, a body member pivotally supported on said cradle means, a barrel means rotatably supported by said body member and carrying elongated spindle means having a portion for supporting a layer of standard test material to engage a test edge, said spindle means being rotatably driven by said barrel means, motor means for rotatably driving said barrel and spindle means at a predetermined velocity, latch means restraining the barrel means against the driving force of said motor means, and means responsive to predetermined pivotal movement of said body member for operating said latch means to release said barrel means for driving rotation thereof by said motor means whereby cutting of said test material determines the presence of edge sharpness exceeding a predetermined safe value.

7. The combination of claim 6 and spring means providing force opposing pivotal movement of said body member and serving to hold said latch means engaged with said barrel means, said spring means permitting the release of said latch means upon predetermined force of engagement between the test material and test edge.

8. The combination of claim 7 and means for adjustably regulating the opposing force of said spring means.

9. The combination of claim 6 and means limiting the rotation of said barrel means.

10. The combination of claim 6 and means for adjustably regulating the rotational velocity of said barrel means comprising friction brake means engaged therewith.

11. The combination of claim 6 in which said motor means comprises a torsion spring anchored to and between said body member and barrel means and operable to effect rotation of said barrel means.

12. The combination of claim 11 and means for energizing said motor means comprising wheel means for rotating said barrel means in a direction appropriate to torque load and torsion spring.

* * * * *

UNITED STATES PATENT OFFICE
CERTIFICATE OF CORRECTION

PATENT NO. : 3,931,732
DATED : January 13, 1976
INVENTOR(S) : Eugene von Heitlinger It is certified that error appears in the above-identified patent and that said Letters Patent are hereby corrected as shown below:

Col. 5, line 14, "registered" should be --registering--.

Col. 5, line 50, "tap" should be --tape--.

Col. 6, line 11, after "the" insert --sharp edge--.

Col. 6, line 12, "heretfore" should be --heretofore--.

Col. 6, line 43, after "described" delete --in--.

Col. 7, line 30, after "at" delete "a".

Col. 8, line 30, after "load" "and" should be --said--.

Signed and Sealed this thirtieth Day of March 1976

[SEAL]

Attest:

RUTH C. MASON
Attesting Officer

C. MARSHALL DANN
Commissioner of Patents and Trademarks